US00PP28136P3

(12) United States Plant Patent
Zaiger et al.

(10) Patent No.: US PP28,136 P3
(45) Date of Patent: Jun. 27, 2017

(54) INTERSPECIFIC TREE NAMED 'ZWEET BETTZEE'

(50) Latin Name: ***Interspecific Prunus* species**
Varietal Denomination: Zweet Bettzee

(71) Applicants: Gary Neil Zaiger, Modesto, CA (US); Leith Marie Gardner, Modesto, CA (US); Grant Gene Zaiger, Modesto, CA (US)

(72) Inventors: Gary Neil Zaiger, Modesto, CA (US); Leith Marie Gardner, Modesto, CA (US); Grant Gene Zaiger, Modesto, CA (US)

( * ) Notice: Subject to any disclaimer, the term of this patent is extended or adjusted under 35 U.S.C. 154(b) by 133 days.

(21) Appl. No.: 14/756,692

(22) Filed: Oct. 1, 2015

(65) Prior Publication Data

US 2017/0099758 P1 Apr. 6, 2017

(51) Int. Cl.
*A01H 5/08* (2006.01)

(52) U.S. Cl.
USPC ..... Plt./180

(58) Field of Classification Search
USPC ..... Plt./156, 180
See application file for complete search history.

*Primary Examiner* — Susan McCormick Ewoldt
*Assistant Examiner* — Karen Redden

(57) ABSTRACT

A new and distinct variety of interspecific tree. The following features of the tree and its fruit are characterized with the tree budded on 'Nemaguard' Rootstock (non-patented), grown on Handford sandy loam soil with Storie Index rating 95, in USDA Hardiness Zone 9, near Modesto, Calif., with standard commercial fruit growing practices, such as pruning, thinning, spraying, irrigation and fertilization. Its novelty consist of the following combination of desirable features:

1. Tree having a vigorous, upright growth habit.
2. Tree being a regular and productive bearer of large size, yellow flesh fruit.
3. Fruit with excellent flavor and eating quality.
4. Fruit with a high degree of soluble solids (Brix) of 20.2°.
5. Fruit with an attractive dark red skin color.

1 Drawing Sheet

Botanical designation: Interspecific *Prunus* species.
Variety denomination: 'Zweet Bettzee'.

BACKGROUND OF THE VARIETY
Field of the Invention

In the field of plant genetics, we conduct an extensive and continuing plant-breeding program including the organization and asexual reproduction of orchard trees, and of which plums, peaches, nectarines, apricots, cherries, almonds and interspecifics are exemplary. It was against this background of our activities that the present variety of interspecific tree was originated and asexually reproduced by us in our experimental orchard located near Modesto, Stanislaus County, Calif.

PRIOR VARIETIES

Among the existing varieties of interspecific trees, which are known to us, and mentioned herein 'Dapple Supreme' Interspecific (U.S. Plant Pat. No. 16,412) and the proprietary non-patented interspecific seedlings '67MD537', '74MF200', '38ZD351', '75LR402', '12MA115' and '76MA672'.

STATEMENT REGARDING FEDERALLY SPONSORED RESEARCH AND DEVELOPMENT

Not applicable.

ORIGIN OF THE VARIETY

The new and distinct variety of interspecific tree was originated by us from crosses of *Prunus salicina* and *Prunus*

*armeniaca* in our experimental orchard located near Modesto, Calif. as a first generation cross between our proprietary non-patented interspecific seedlings '67MD537' and '74MF200'. The seed parent '67MD537' is a first generation seedling cross from our proprietary non-patented interspecific seedlings '38ZD351' and '75LR402'. The pollen parent '74MF200' originated as a first generation cross between our proprietary non-patented interspecific seedlings '12MA115' and '76MA672'. A large number of these first generation seedlings were budded onto older established trees of 'Nemaguard' Rootstock (non-patented) to enhance earlier fruit production. Under close and careful observation the present budded seedling exhibited desirable fruit and tree characteristics and was selected in 2012 for additional asexual propagation and commercialization.

ASEXUAL REPRODUCTION OF THE VARIETY

In 2012 asexual reproduction of the new and distinct variety of interspecific tree was by budding to 'Nemaguard' Rootstock (non-patented), as performed by us in our experimental orchard located near Modesto, Calif., and shows that reproductions run true to the original tree and all characteristics of the tree and its fruit are established and transmitted through succeeding asexual propagations.

SUMMARY OF THE NEW VARIETY

A new and distinct variety of interspecific tree, which consists of Plum and Apricot has vigorous, upright growth and is a regular and productive bearer of large size fruit with an attractive dark red skin color. The fruit is further characterized by its firm flesh, excellent flavor and eating quality with good storage and shipping ability. In comparison to its seed parent (67MD537) the fruit of the new variety has dark red skin compared to yellow. In comparison to its pollen parent (74MF200) the fruit of the new variety has yellow flesh compared to white and is approximately 10 days earlier in maturity. In comparison to the commercial variety 'Dapple Supreme' Interspecific (U.S. Plant Pat. No. 16,412) the fruit of the new variety has yellow flesh compared to red and a higher degree of soluble solids (Brix) of 20.2°.

DESCRIPTION OF THE PHOTOGRAPH

The accompanying color photographic illustration shows typical specimens of the foliage and fruit of the present new interspecific variety.

The illustration shows the upper and lower surface of the leaves, an exterior and sectional view of a single fruit divided in its suture plane to show flesh color, pit cavity and the stone remaining in place.

The photographic illustration was taken shortly after being picked (shipping ripe) from a 5 year old tree and the colors are as nearly true as is reasonably possible in a color representation of this type.

DESCRIPTION OF THE VARIETY

The following is a detailed botanical description of the new variety of interspecific tree, its flowers, foliage and fruit, as based on observations of 5 year old specimens grown near Modesto, Calif., with color in accordance with Munsell Book of Color published in 1958.

Tree:

*Size.*—Large, pruned to 3 to 3.5 meters in height and width for economical harvesting of fruit. Varies with different cultural practices.

*Vigor.*—Vigorous, tree growth of 1.5 to 2 meters the first growing season. Varies with cultural practices, soil type, fertility and climatic conditions.

*Form.*—Upright, usually pruned to vase shape.

*Branch habit.*—Upright, crotch angle approximately 30°, increases with heavy crop load.

*Productivity.*—Productive, thinning and spacing of fruit necessary for marketable size fruit. Number of fruit set varies with climatic conditions during blooming period.

*Bearer.*—Regular, has had adequate fruit set 3 consecutive years. No alternate bearing observed.

*Fertility.*—Self-sterile, pollinator required.

*Density.*—Medium dense, usually pruned to vase shape to increase air movement and sunlight to enhance fruit color and health of fruit spurs.

*Hardiness.*—Hardy in all stone fruit growing areas of California. Tree grown in USDA Hardiness Zone 9. Winter chilling requirement approximately 800 hours at or below 45° F.

Trunk:

*Size.*—Large, average circumference 61.0 cm at 25.4 cm above ground on a 5 year old tree.

*Stocky.*—Medium stocky.

*Texture.*—Medium shaggy, roughness increases with age.

*Color.*—Varies from 5Y 5/2 to 7.5Y 6/2.

Branches:

*Size.*—Medium. Average circumference 14.5 cm at 1.2 meters above ground. Crotch angle approximately 30°, increases with heavy crop load.

*Surface texture.*—New growth relatively smooth. Mature growth medium rough, roughness increases with age.

*Lenticels.*—Average number 66 in a 25.8 square cm section of branch. Average length 3.6 mm. Average width 1.6 mm. Color varies from 10YR 6/10 to 10YR 5/8.

*Color.*—New growth varies from 2.5GY 5/8 to 5GY 5/8. Mature growth varies from 7.5YR 3/6 to 10YR 3/6, varies with age of growth.

Leaves:

*Size.*—Medium to large. Average length 102.8 mm. Average width 47.7 mm.

*Form.*—Oblanceolate.

*Apex.*—Acuminate.

*Base.*—Cuneate.

*Margin.*—Doubly serrate.

*Thickness.*—Medium.

*Surface texture.*—Upper surface relatively smooth, slight indentations over midrib and leaf veins. Lower surface relatively smooth except for small ridges created by midrib and pinnate venation. Both upper and lower surfaces glabrous.

*Petiole.*—Small to medium. Average length 13.7 mm. Average width 1.7 mm. Surface — glabrous. Longitudinally grooved. Color varies from 5GY 6/8 to 5R 2/6.

*Glands.*—Type — globose. Size — small. Average length 0.6 mm. Average diameter 0.4 mm. Number varies from 3 to 5, average number 4. Located primarily on the upper portion of the petiole and base of leaf blade. Color 5GY 6/8.

*Stipules.*—Average number 2. Average length 5.0 mm. Margin — pectinate. Color varies from 5GY 6/6 to 5R 2/6.

*Color.*—Upper surface 2.5GY 3/2 to 5GY 3/6. Lower surface varies from 7.5GY 3/4 to 5GY 3/6. Midvein color varies from 5GY 5/6 to 5GY 6/6.

Flower buds:

*Size.*—Small to medium. Average length 7.9 mm. Average diameter 4.6 mm.

*Hardiness.*—Hardy with respect to California winters.

*Density.*—Very dense.

*Form.*—Conical, becoming elongated just before opening.

*Pedicel.*—Average length 10.1 mm. Average width 0.8 mm. Surface — glabrous. Color varies from 5GY 7/10 to 5GY 6/8.

*Color.*—N 9.5/(white).

*Number of buds per spur.*—Varies from 5 to 9, average number 7.

Flowers:

*Blooming period.*—Date of First Bloom Feb. 16, 2015. Date of Petal Fall Feb. 26, 2015, varies slightly with climatic conditions.

*Size.*—Small to medium. Average height 11.0 mm. Average diameter 18.0 mm.

*Petals.*—Normally 5, alternately arranged to sepals. Petal apex — rounded. Petal base — truncate. Size — small. Average length 9.0 mm. Average width 6.8 mm. Form — globose to elliptical.

Arrangement — free. Margin — sinuate. Color N 9.5/(white). Both upper and lower surfaces glabrous.

*Sepals.*—Normally 5, alternately arranged to petals. Size — small. Average length 2.9 mm. Average width 2.8 mm. Shape — triangular. Apex rounded to triangular. Margin — entire. Both upper and lower surfaces glabrous. Color — upper surface varies from 5GY 7/12 to 5GY 6/8. Lower surface varies from 5GY 6/8 to 5GY 5/10.

*Stamens.*—Average number per flower 31. Average filament length 8.2 mm. On average the stamens are above the height of the petals. Filament color N 9.5/(white). Anther color varies from 10R4/10 to 5Y 8/8.

*Pollen.*—Self-sterile, pollinator required. Color varies from 2.5Y 7/12 to 5Y 7/12.

*Pistil.*—Number — normally 1. Surface — glabrous. Average length 8.7 m. Position of stigma an average of 1.1 mm below anthers. Color varies from 10Y 8.5/4 to 2.5GY 8/4.

*Fragrance.*—Moderate.

*Color.*—N 9.5/(white).

*Pedicel.*—Average length 11.8 mm. Average width 0.8 mm. Color varies from 5GY 7/8 to 5GY 5/10.

*Number flowers per flower bud.*—Average number 2, varies from 1 to 3.

Fruit:

*Maturity when described.*—Firm ripe and ready for consumption.

*Date of first picking.*—Jun. 22, 2015.

*Date of last picking.*—Jul. 2, 2015, varies slightly with climatic conditions.

*Size.*—Large. Average diameter axially 57.6 mm. Average transversely in suture plane 64.7 mm. Average weight 142.0 grams, varies slightly with fertility of the soil, amount of thinning and climatic conditions.

*Form.*—Globose.

*Suture.*—Nearly smooth, extends from base to apex.

*Ventral surface.*—Smooth.

*Apex.*—Rounded.

*Base.*—Flat.

*Stem cavity.*—Rounded to slightly elongated in suture plane. Average depth 8.4 mm. Average diameter 3.7 mm.

Stem:

*Size.*—Medium. Average length 12.4 mm. Average diameter 2.1 mm.

*Color.*—Varies from 2.5GY 6/10 to 10Y 6/8.

Flesh:

*Ripens.*—Evenly.

*Texture.*—Firm, meaty.

*Fibers.*—Few, small, tender.

*Firmness.*—Firm, comparable to other commercial interspecific varieties.

*Aroma.*—Moderate.

*Amydgalin.*—Undetected.

*Eating quality.*—Excellent.

*Flavor.*—Excellent, good balance between acid and sugar.

*Juice.*—Heavy amount, enhances flavor.

*Acidity.*—Not available.

*Brix.*—Average Brix 20.2°, varies slightly with amount of fruit per tree and climatic conditions.

*Color.*—Varies from 5Y 6/6 to 5Y 7/4.

*Pit cavity.*—Average length 29.2 mm. Average width 22.1 mm. Average depth 6.8 mm. Color varies from 10YR 5/6 to 10YR 5/8.

Skin:

*Thickness.*—Medium.

*Surface.*—Smooth.

*Bloom.*—Moderate amount, complete coverage.

*Tendency to crack.*—None.

*Color.*—Ground color varies from 5Y 6/6 to 2.5Y 6/6. Overspread with 10R 3/6 to 10R 3/8.

*Tenacity.*—Tenacious to the flesh.

*Astringency.*—Slight to none.

Stone:

*Type.*—Clingstone, medium adherence to flesh.

*Size.*—Medium. Average length 28.2 mm. Average width 21.1 mm. Average thickness 11.6 mm.

*Form.*—Obovoid.

*Base.*—Flat.

*Apex.*—Rounded.

*Surface.*—Pitted throughout.

*Sides.*—Unequal, one side extending further from suture plane.

*Ridges.*—Very narrow, small ridge near groove on each side of suture, extends from base to apex.

*Tendency to split.*—None.

*Color.*—Varies from 5YR 4/8 to 7.5YR 5/8 when dry.

Kernel:

*Size.*—Small to medium. Average length 15.0 mm. Average width 11.0 mm. Average depth 5.7 mm.

*Form.*—Ovate.

*Viability.*—Viable, complete embryo development.

*Skin color.*—Varies from 2.5Y 8/8 to 5Y 8/8.

Use: Dessert.

*Market.*—Local and long distance.

Keeping quality: Good, held firm in cold storage for 3 weeks at 38° to 42° F. without internal breakdown of flesh or appreciable loss of eating quality.

Shipping quality: Good, showed minimal skin scarring or flesh bruising during picking, packing and shipping trials.

Plant/fruit disease resistance/susceptibility: No specific testing for relative plant/fruit disease resistance/susceptibility has been designed. Under close observation during planting, growing and harvesting of fruit, under normal cultural and growing conditions near Modesto, Calif., no particular plant/fruit disease resistance or susceptibility has been observed. Any variety observed during indexing of plant characteristics with abnormal fungus, bacterial, virus or insect susceptibility is destroyed and eliminated from our breeding program. No atypical resistances/susceptibilities have been noted under normal cultural practices. The present new variety of interspecific tree, its flowers foliage and fruit herein described may vary in slight detail due to climate, soil conditions and cultural practices under which the variety may be grown. The present description is that of the variety grown under the ecological conditions prevailing near Modesto, Calif.

The invention claimed is:

1. A new and distinct variety of interspecific tree, substantially as illustrated and described.

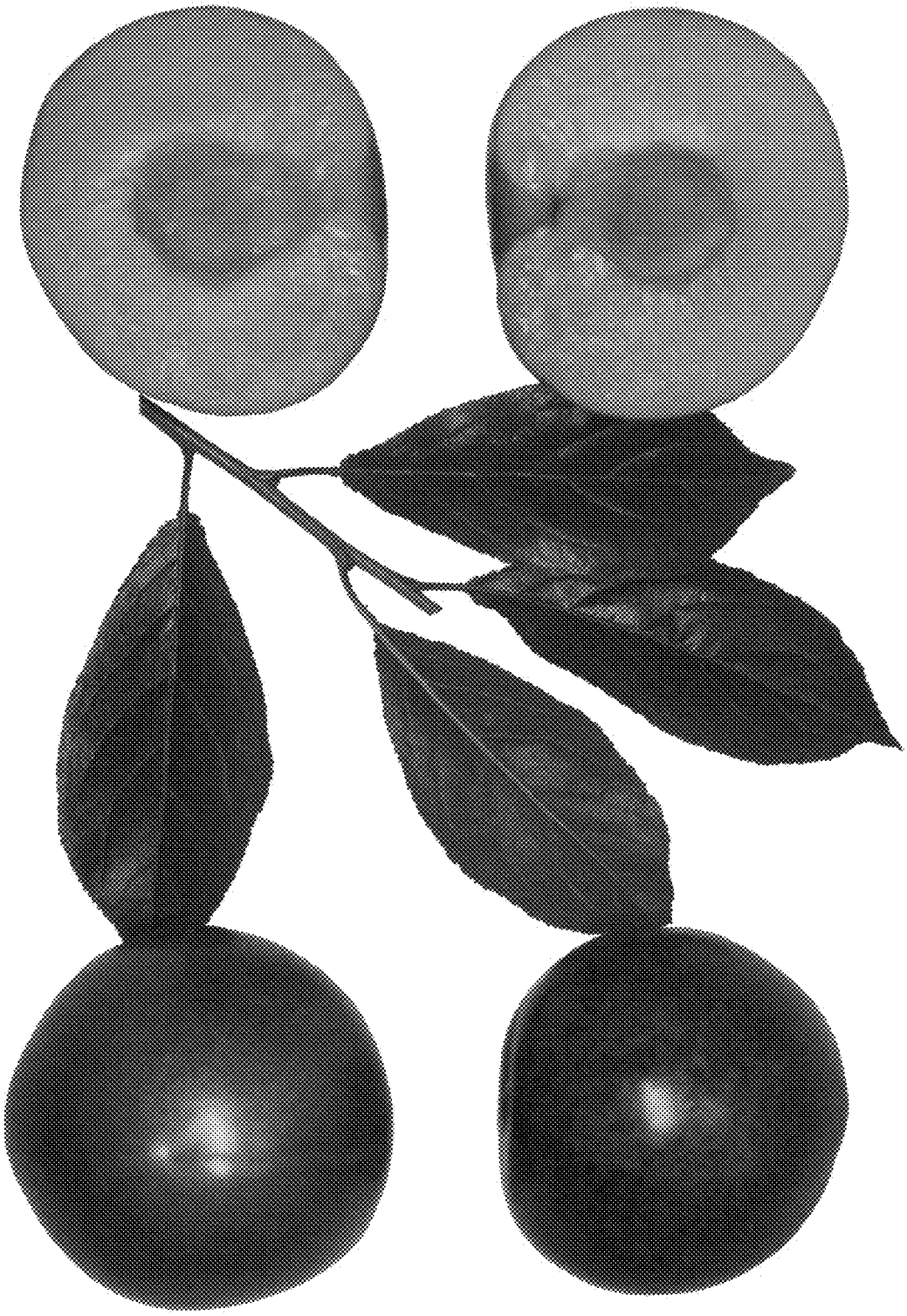

* * * * *